(12) United States Patent
Tsukamoto

(10) Patent No.: US 8,911,629 B2
(45) Date of Patent: *Dec. 16, 2014

(54) DIALYSATE REGENERATION SYSTEM FOR PORTABLE HUMAN DIALYSIS

(75) Inventor: Takuji Tsukamoto, Beaverton, OR (US)

(73) Assignee: Chemica Technologies, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/195,719

(22) Filed: Aug. 1, 2011

(65) Prior Publication Data

US 2012/0018377 A1 Jan. 26, 2012

Related U.S. Application Data

(60) Continuation of application No. 12/233,912, filed on Sep. 19, 2008, now Pat. No. 7,988,854, which is a division of application No. 11/020,841, filed on Dec. 22, 2004, now Pat. No. 7,435,342.

(60) Provisional application No. 60/532,759, filed on Dec. 24, 2003.

(51) Int. Cl.
*B01D 61/26* (2006.01)
*B01D 61/30* (2006.01)
*B01D 61/24* (2006.01)
*A61M 1/16* (2006.01)
*B01D 61/28* (2006.01)

(52) U.S. Cl.
CPC ............. *A61M 1/1696* (2013.01); *B01D 61/30* (2013.01); *B01D 2311/06* (2013.01); *B01D 61/243* (2013.01)
USPC ...... 210/646; 210/321.71; 210/645; 435/177; 554/132

(58) Field of Classification Search
None
See application file for complete search history.

(56) References Cited

U.S. PATENT DOCUMENTS

| | | | |
|---|---|---|---|
| 3,268,441 A | 8/1966 | Lindstrom | |
| 3,463,728 A | 8/1969 | Kolobow et al. | |
| 3,506,126 A | 4/1970 | Serfass et al. | |
| 3,608,729 A | 9/1971 | Haselden | |

(Continued)

FOREIGN PATENT DOCUMENTS

| | | | |
|---|---|---|---|
| JP | 53126797 A | 11/1978 | |
| JP | 54098095 A | 8/1979 | |

(Continued)

OTHER PUBLICATIONS

Blumenkrantz et al. "Applications of the Redy® Sorbent System to Hemodialysis and Peritoneal Dialysis." Artificial Organs. 3.3 (1979): 230-236.

(Continued)

*Primary Examiner* — Krishnan S Menon
(74) *Attorney, Agent, or Firm* — Alleman Hall McCoy Russell & Tuttle LLP

(57) ABSTRACT

A dialysate regeneration chamber is provided. In one embodiment, the dialysate regeneration chamber may include a toxin trap configured to selectively trap toxins and repel select cations. In another embodiment, generating a toxin trap may include oxidizing an activated carbon fiber and attaching a fatty acid to the oxidized activated carbon fiber to generate an ion-selective barrier, wherein the fatty acid extends away from the activated carbon fiber.

17 Claims, 5 Drawing Sheets

(56) References Cited

U.S. PATENT DOCUMENTS

| | | | |
|---|---|---|---|
| 3,617,545 A | 11/1971 | Dubois et al. | |
| 3,994,799 A | 11/1976 | Yao et al. | |
| 4,031,010 A | 6/1977 | Nose | |
| 4,083,777 A | 4/1978 | Hutchisson | |
| 4,094,775 A | 6/1978 | Mueller | |
| 4,134,834 A | 1/1979 | Brous | |
| 4,192,748 A | 3/1980 | Hyden | |
| 4,212,738 A | 7/1980 | Henne | |
| 4,213,859 A | 7/1980 | Smakman et al. | |
| 4,248,736 A | 2/1981 | Fuchigami et al. | |
| 4,252,653 A * | 2/1981 | Beck et al. | 210/321.87 |
| 4,267,047 A | 5/1981 | Henne et al. | |
| 4,269,708 A | 5/1981 | Bonomini et al. | |
| 4,276,175 A | 6/1981 | Bower | |
| 4,293,418 A | 10/1981 | Fujii et al. | |
| 4,323,445 A | 4/1982 | Alekhin et al. | |
| 4,388,163 A | 6/1983 | Richter et al. | |
| 4,460,555 A | 7/1984 | Thompson | |
| 4,473,449 A | 9/1984 | Michaels et al. | |
| 4,508,851 A * | 4/1985 | Izumi et al. | 502/426 |
| 4,581,141 A | 4/1986 | Ash | |
| 4,650,587 A | 3/1987 | Polak et al. | |
| 4,661,246 A | 4/1987 | Ash | |
| 4,663,006 A | 5/1987 | Yao et al. | |
| 4,726,381 A | 2/1988 | Jones | |
| 4,763,658 A | 8/1988 | Jones | |
| 4,765,339 A | 8/1988 | Jones | |
| 4,774,955 A | 10/1988 | Jones | |
| 4,832,839 A | 5/1989 | Tamura | |
| 4,846,950 A | 7/1989 | Yao et al. | |
| 4,897,200 A | 1/1990 | Smakman | |
| 4,950,224 A | 8/1990 | Gorsuch et al. | |
| 5,084,349 A | 1/1992 | Sasaki et al. | |
| 5,151,082 A | 9/1992 | Gorsuch et al. | |
| 5,227,820 A | 7/1993 | Miyashita et al. | |
| 5,312,547 A | 5/1994 | Kruger et al. | |
| 5,336,165 A | 8/1994 | Twardowski | |
| 5,368,555 A | 11/1994 | Sussman et al. | |
| 5,405,766 A * | 4/1995 | Kallury et al. | 435/174 |
| 5,423,738 A | 6/1995 | Robinson et al. | |
| 5,484,397 A | 1/1996 | Twardowski | |
| 5,545,131 A | 8/1996 | Davankov | |
| 5,679,231 A | 10/1997 | Alexander et al. | |
| 5,744,042 A | 4/1998 | Stange et al. | |
| 5,824,213 A | 10/1998 | Utterberg | |
| 5,868,936 A | 2/1999 | Ofsthun et al. | |
| 5,871,649 A | 2/1999 | Ofsthun et al. | |
| 5,895,571 A | 4/1999 | Utterberg | |
| 5,902,476 A | 5/1999 | Twardowski | |
| 5,919,369 A | 7/1999 | Ash | |
| 5,942,112 A | 8/1999 | Ishak | |
| 5,944,684 A | 8/1999 | Roberts et al. | |
| 5,980,481 A | 11/1999 | Gorsuch | |
| 6,099,737 A | 8/2000 | Sherman et al. | |
| 6,129,699 A | 10/2000 | Haight et al. | |
| 6,132,616 A | 10/2000 | Twardowski et al. | |
| 6,146,536 A | 11/2000 | Twardowski | |
| 6,228,047 B1 | 5/2001 | Dadson | |
| 6,234,992 B1 | 5/2001 | Haight et al. | |
| 6,260,715 B1 | 7/2001 | Simard et al. | |
| 6,332,985 B1 | 12/2001 | Sherman et al. | |
| 6,395,180 B2 | 5/2002 | Chioini et al. | |
| 6,423,024 B1 | 7/2002 | Strom et al. | |
| 6,472,200 B1 | 10/2002 | Mitrani | |
| 6,561,996 B1 | 5/2003 | Gorsuch | |
| 6,579,460 B1 | 6/2003 | Willis et al. | |
| 6,582,385 B2 | 6/2003 | Burbank et al. | |
| 6,589,482 B1 | 7/2003 | Burbank et al. | |
| 6,595,943 B1 | 7/2003 | Burbank | |
| 6,623,638 B2 | 9/2003 | Watkins et al. | |
| 6,638,264 B1 | 10/2003 | Tryggvason et al. | |
| 6,638,477 B1 | 10/2003 | Treu et al. | |
| 6,638,478 B1 | 10/2003 | Treu et al. | |
| 6,824,689 B2 | 11/2004 | Wang et al. | |
| 7,122,378 B1 * | 10/2006 | Akita et al. | 436/94 |
| 2003/0105424 A1 | 6/2003 | Karoor et al. | |
| 2007/0122893 A1 * | 5/2007 | Sato et al. | 435/182 |

FOREIGN PATENT DOCUMENTS

| | | | |
|---|---|---|---|
| JP | 55045437 A | | 3/1980 |
| JP | 55122559 A | | 9/1980 |
| JP | 56045193 A | * | 4/1981 |
| JP | 56051237 A | | 5/1981 |
| JP | 56057452 A | | 5/1981 |
| JP | 56105756 A | | 8/1981 |
| JP | 01307456 A | | 12/1989 |

OTHER PUBLICATIONS

Chen and Chiu. "A poly (N-isopropylacrylamide-co-N-acryloxysuccinimide-co-2-hydroxyethyl methacrylate) composite hydrogel membrance for urease immobilization to enhance urea hydrolysis rate by temperature swing." Enzyme and Microbial Technology. 26 (2000): 359-367.

Economy and Lin. "Adsorption Characteristics of Activated Carbon Fibers." Appl. Polym. Symp. 29 (1976): 199-211.

Elçin and Elçin. "Polycation-Coated Polyanion Microspheres of Urease for Urea Hydrolysis." Art. Cells, Blood Subs., Immob. Biotech. 28.1 (2000): 95-111.

Galons et al. "Hemodialysis Increases Apparent Diffusion Coefficient of Brain Water in Nephrectomized Rats Measured by Isotropic Diffusion-weighted Magnetic Resonance Imaging." J. Clin. Invest. 98.3 (1996): 750-755.

Hamarat and Uslan. "Immobilization of Urease on Activated Methoxypolyethyleneglycol-5000." Art. Cells, Blood Subs., Immob. Biotech. 24.3 (1996): 273-283.

Hayes. "Novoloid Fibers." Kirk-Othmer: Encyclopedia of Chemical Technology. vol. 16, Third Edition. Hoboken, New Jersey: John Wiley & Sons, Inc., 1981. 125-138.

Hayes. "Novoloid and Related Fibers in Nonwoven Structures." Index 93 Congress Papers 2C (1993): 1-24.

Henderson. "Future Developments in the Treatment of End-Stage Renal Disease: A North American Perspective." Amer. Journal of Kidney Disease 35.4 Suppl. 1 (2000): S106-S116.

Keshaviah. "Technological Aspects of Hemodialysis and Peritoneal Dialysis." Clinical Dialysis. 3rd ed. Nissenson et al., eds. Norwalk, Connecticut: Appleton & Lange (1995). 46-75.

Kibarer et al. "Interesting Features of an Activated Carbon Supported Urease System." Artif. Organs. 18.3 (1994): 222-226.

Koncki et al. "Enzyme biosensor for urea based on a novel pH bulk optode membrane." Biosensors & Bioelectronics. 10 (1995): 653-659.

Pimenov et al. "Accelerated Adsorption with Activated Carbon Fiber." Separation Science and Technol. 30.16 (1995): 3183-3194.

Shapiro. "Sorbent Dialysis." Nissenson et al. (eds.), Clinical Dialysis. 3rd ed. Nissenson et al., eds. Norwalk, Connecticut: Appleton & Lange (1995). 898-905.

Sherif et al. "Advantages of Using Non-isothermal Bioreactors in Agricultural Waste Water Treatment by Means of Immobilized Urease. Study on the Influence of Spacer Length and Immobilization Method." J. Agric. Food Chem. 50 (2002): 2802-2811.

Shettigar. "Innovative Extracorporeal Membrane Systems." J. Membrane Sci. 44 (1989): 89-114.

Yeun and Depner. "Principles and Practice of Hemodialysis." Dialysis and Transplantation. Owen and Pereira, eds. Philadelphia: W.B. Saunders Company (2000). 1-31.

Yeun and Kaysen. "C-Reactive protein, oxidative stress, homocysteine, and troponin as inflammatory and metabolic predictors of atherosclerosis in ESRD." Curr. Opin. Nephrol. Hypertens. 9 (2000): 621-630.

Office action of corresponding Japanese Application No. 2006-547442, Issued Aug. 31, 2010, Japanese Patent and Trademark Office, 5 pages.

(56) References Cited

OTHER PUBLICATIONS

Nissenson, Allen R. et al., "Clinical Dialysis," Third Edition, Norwalk, Connecticut: Appleton & Lange, 1995, 11 pages.

ISA European Patent Office, Supplementary European Search Report of EP04817056.7, Aug. 28, 2012, WIPO, 5 pages.
Korean Intellectual Property Office, Office Action of Korean Patent Application No. 10-20067010928, Sep. 26, 2012, Korea, 4 pages.

* cited by examiner

DIALYSATE REGENERATION SYSTEM FOR PORTABLE HUMAN DIALYSIS

CROSS-REFERENCE TO RELATED APPLICATIONS

This application is a continuation of U.S. Patent Application No. 12/233,912, filed Sep. 19, 2008, now issued as U.S. Pat. No. 7,988,854, which is a divisional of U.S. Patent Application No. 11/020,841, filed Dec. 22, 2004, now issued as U.S. Pat. No. 7,435,342, which claims the benefit of U.S. Provisional Patent Application No. 60/532,759, filed Dec. 24, 2003. The above applications are hereby incorporated by reference in their entirety for all purposes. The invention described in this application was made in part under grant #H133S030019 from the Department of Education. (Authority: 20 U.S.C. 1221e-3 and 3474).

TECHNICAL FIELD

The present disclosure relates generally to apparatus, systems and methods related to dialysis systems.

BACKGROUND

With renal failure, physiological disturbance may occur within an animal system. Such disturbances may include failure of the system to fully excrete various body toxins and failure of the system to maintain homeostasis of water and required minerals. Dialysis treatments may be used to compensate for such renal failure.

Two types of dialysis therapies are commonly available, hemodialysis and peritoneal dialysis. Hemodialysis treatments typically utilize a hemodialysis machine, which operates as an external artificial kidney, to separate body toxins from the blood. A patient may be coupled to the hemodialysis machine by insertion of catheters into the patient's veins and arteries thus coupling the patient to the machine such that the patient's blood flow to and from the hemodialysis machine. In the hemodialysis machine, the blood engages a dialysate into which the blood toxins are transferred.

Peritoneal dialysis cleans the blood without removing the blood to an external system. Briefly, with peritoneal dialysis, a dialysate may be infused into a patient's peritoneal cavity through a catheter implanted in the cavity. The dialysis solution contacts the patient's peritoneal membrane and waste, toxins and excess water pass from the patient's bloodstream through the peritoneal membrane and into the dialysate. The transfer of the waste, toxins and water from the bloodstream into the dialysate occurs due to diffusion and osmosis, i.e., an osmotic gradient occurs across the membrane. The spent dialysate may drain from the patient's peritoneal cavity, removing the waste, toxins and excess water, from the patient. The cycle is repeated as necessary.

In a typical hemodialysis machine, blood may be separated from surrounding dialysate solution by a semi-permeable membrane. The membrane contains pores which may allow substances in normal molecular solution and the solvent to pass through the membrane, but it may be configured to prevent the passage of large molecules, such as high molecular weight proteins and cellular constituents of the blood. The membrane further may prevent the passage of bacteria. Since the apparatus operates by diffusion and osmosis, the dialysate solution, also referred to generally as dialysate, typically contains physiological concentrations of some membrane-passing dissolved normal constituents of the blood, such as various electrolytes. The dialysate also may include various concentrations of substances which may be desired to be introduced into the blood stream by diffusion, such as drugs, dextrose, etc.

In addition to the above membrane, the typical hemodialysis machine may include various pumps and sensors. Pumps, or bubblers, may be utilized to introduce oxygen into the dialysate so as to maintain the oxygen content of the blood in normal condition. Pumps may also regulate blood flow. Moreover, pumps may be provided to introduce additional substances, such as anticoagulants, into the blood. Pumped anticoagulants, such as heparin or citrate, may prevent clotting of the blood on surfaces that are in contact with the blood. In addition, the machines may include sensors, such as temperature sensors as well as heaters to maintain the dialysate at substantially the same temperature as the blood.

Although effective, a patient must adjust to various complications presented by dialysis treatment. For example, patients may have to travel to a dialysis treatment facility, such as a hospital or clinic, for the dialysis treatment. Since dialysis typically is required on a schedule, such as three or more treatments a week, such visits to the dialysis treatment facility may be time-consuming and limiting to a patient. For example, the dialysis treatments may limit a patient's ability to easily travel. For example, patients who select to travel may have to prearrange for a visit at a different facility. Such arrangements may be difficult, thus making travel for a dialysis patient complicated.

In some situations, dialysis treatments may be performed at home. Although, such home situations may be more convenient, the equipment may be of substantial size which may cause an inconvenience to the patient. Further additional equipment, such as a water purification system may be required. The water purification system may further complicate the process and require additional room further complicating home dialysis treatments.

It should be appreciated that typical dialysis machines may be of such a size to prevent portability. For example, some dialysis machines are substantially the size of a refrigerator, thus preventing easy portability. The lack of portability of such dialysis machines may limit life choices for a dialysis patient. For example, many dialysis patients, whether using home treatment or a dialysis treatment facility have to limit travel and other opportunities due to the required time and the limited choices for their treatments. It is noted that the time required for hemodialysis may vary. For example, in some systems, hemodialysis treatment may last about four hours. This substantial period of time and the necessity to use a treatment facility or a home-based non-portable unit prevents a patient from traveling, etc.

In addition to the time required for such dialysis treatments, the cost of dialysis provide additional complications, for the patient, the treatment facilities, health insurance companies, Medicare, etc. For example, treatment facilities have large expenses for maintaining and staffing the treatment facility.

In addition, the costs of dialysis itself may be expensive. In addition to the cost of the dialysis machines, recurring costs for dialysate and environmental waste may be cost prohibitive. For example, in conventional hemodialysis, a large amount of dialysate, for example about 120 liters, is used to dialyze the blood during a single hemodialysis therapy. The spent dialysate is then discarded. The large amount of used dialysate may increase the costs of dialysis. Additionally, costs may be increased due to the large amounts of purified water that are needed. For example, costs may be increased due to equipment to generate, store and use purified water.

Further, such dialysate, needles, and other medically-contaminated products, must be appropriately discarded, which may further increase costs of and time associated with dialysis treatment.

SUMMARY

A dialysate regeneration chamber is provided. In one embodiment, the dialysate regeneration chamber may include a toxin trap configured to selectively trap toxins, and repel select cations. In another embodiment, generating a toxin trap may include oxidizing an activated carbon fiber and attaching a fatty acid to the oxidized activated carbon fiber to generate an ion-selective barrier, wherein the fatty acid extends away from the activated carbon fiber.

BRIEF DESCRIPTION OF THE DRAWINGS

The disclosure is illustrated by way of example and not by way of limitation in the figures of the accompanying drawings, in which the like references indicate similar elements and in which.

DETAILED DESCRIPTION

Figure 1:
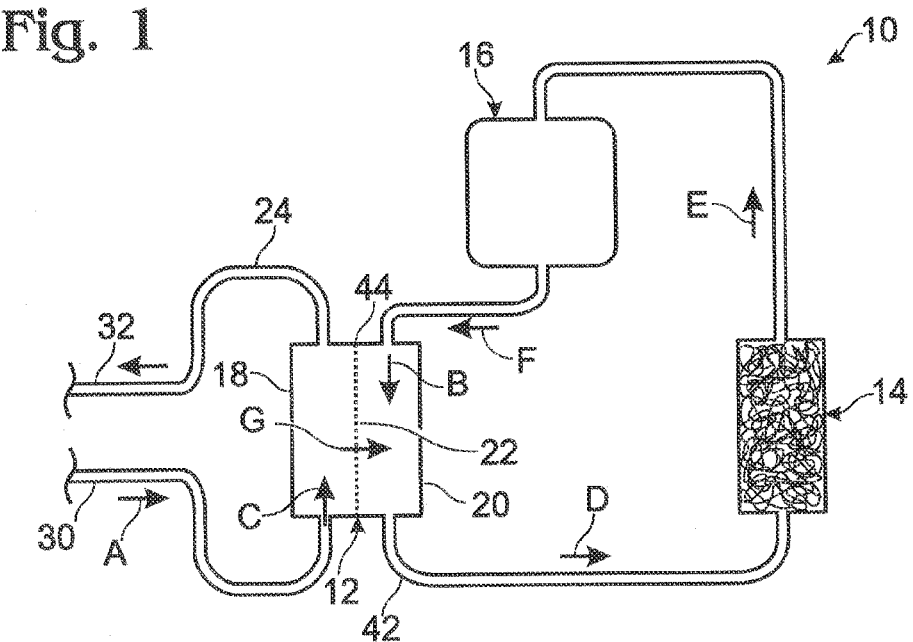
FIG. 1 is a schematic illustration of an exemplary dialysis system in accordance with the present disclosure.

An exemplary dialysis system for use in dialysis is illustrated at 10 in FIG. 1. The dialysis system may include a dialysis chamber 12 and a dialysate regeneration chamber or dialysate regeneration cartridge 14. Briefly, dialysis chamber 12 may include a blood compartment and a dialysate compartment. Toxins may be transferred from the blood to dialysate due to diffusion and osmosis across the semi-permeable membrane separating the two compartments. The transferred toxins may saturate the dialysate in the dialysate compartment. Saturate, as used herein, includes any level of increased toxin, such that saturated dialysate is dialysate with an increased toxin level.

The saturated dialysate also referred to as spent dialysate may be directed into regeneration chamber 14 which may be configured to separate toxins from the spent dialysate. Once the toxins are removed from the spent dialysate, the dialysate may be considered refreshed and reused. A dialysate reservoir 16 may be provided to store purified dialysate and refreshed dialysate for use during the dialysis process.

It should be appreciated that although dialysis chamber 12, regeneration chamber 14 and reservoir 16 are shown as separate devices linked through couplers, such as tubing system 24, one or more the chambers and/or reservoir may be integrated together. Typically, the regeneration chamber is disposed intermediate the dialysis chamber and the reservoir, however other configurations may be possible.

As described briefly above, dialysis chamber 12 of the exemplary embodiment may be subdivided into a blood compartment 18 and a dialysate compartment 20. Blood compartment 18 may be separated from dialysate compartment 20 via a semi-permeable membrane 22. Blood, or any other suitable fluid, may be introduced into dialysis chamber 12 via inflow 30. Inflow 30 may be a blood inflow coupled to a patient's body, such that blood flows from the patient's body into blood compartment 18 in the direction of arrow A. Blood may flow into and through blood compartment 18 in the direction of arrow C. Blood may return to the patient's body through outflow 32.

The blood inflow 30 and the blood outflow 32 may include tubing system 24 (as shown in this embodiment), or any other conduit connecting the fluid source (such as the patient) to the dialysis chamber. Various pumps may be provided to enable flow into and out of the dialysis chamber. In some embodiments, the blood inflow and blood outflow may be incorporated in a dual-lumen device that permits bidirectional flow into and out of the blood compartment.

Dialysate, also referred to as dialysis fluid, may enter dialysate chamber 12 and flow through the dialysate chamber in the direction of arrow B. As described above, the dialysate typically includes physiological concentrations of membrane-permeable, dissolved normal constituents of the blood. The dialysate also may include various concentrations of substances that are desired to be introduced into the blood stream by diffusion such as select drugs, sugars, etc. Additionally, in some embodiments, oxygen may be bubbled into the dialysate.

While in the dialysis chamber 12, blood may be separated from dialysate by semi-permeable membrane 22. Semi-permeable membrane 22 may be any commercially available dialyzer membrane obtained from a standard dialyzer manufacturer. The typical dialyzer membrane, or semi-permeable membrane utilized in the dialysis system may allow substances in normal molecular solution and small molecules to pass through permeable pores, while preventing the passage of large molecules, such as bacteria, high-molecular proteins, and cellular constituents of the blood.

In some embodiments, semi-permeable membrane 22 may have a large surface area which may accommodate increased osmotic interchange between the blood and the dialysate. For example, blood may be distributed such that it flows along the membrane ensuring maximum contact with the semi-permeable membrane bathed by dialysate. It should be appreciated that other suitable flow mechanisms and configurations for contact and engagement with the semi-permeable membrane may be used.

Semi-permeable membrane 22 of dialysis chamber 12 may be permeable to system waste materials, including, but not limited to, urea, uric acid, creatinine, phosphate and other small organic waste molecules. As used herein, system waste materials may be referred to generally as toxins. Thus, the various toxins carried in the blood may diffuse across semi-permeable membrane 22 (in the direction of arrow G), and mix with the dialysate contained within the dialysate compartment 20 of dialysis chamber 12.

Upon the receipt of the toxins, the concentration of the toxin molecules increase in the dialysate, and the concentration differential between the blood in blood compartment 18 and the dialysate in dialysate compartment 20, is reduced. Accordingly, when the dialysate contains a concentration of the toxins (such that the dialysate has an increased toxin level), the dialysate may be considered spent dialysate. The spent dialysate may not be as efficient in removing additional toxins from the blood across semi-permeable membrane 22 via diffusion. Thus, the spent dialysate may flow or be pumped such that the spent dialysate exits the dialysate chamber 12 through dialysate outflow 42.

Many currently available hemodialysis machines dispose of the spent dialysate. As an example, in some currently used hemodialysis systems, a patient's blood is pumped through a hemodialysis machine, via catheters inserted into the patient's veins and arteries, connecting the blood flow to and from the hemodialysis machine. As blood passes through the hemodialysis machine, toxins and excess water are removed from the patient's blood by diffusion across a semi-permeable membrane to a dialysate. The spent dialysate or waste may then be discarded.

In some systems, the semi-permeable membrane may be permeable to a variety of small organic molecules, such that some important small organic molecules are lost from the blood.

Many of these currently available hemodialysis treatment machines utilize a large amount of dialysate because the spent dialysate is discarded after one pass through the dialyzer. In a single hemodialysis therapy, 120 liters of dialysate may be consumed to dialyze the patient's blood. One of the consequences of this large dialysate volume requirement is the lack of portability of the dialysis machines. Hemodialysis treatments are thus commonly administered in specialized dialysis treatment facilities. Additional disadvantages include various environmental and financial concerns which result from the disposal of the large volumes of spent dialysate.

Referring back to FIG. 1, the dialysis system 10 may eliminate the need for such a large volume of dialysate by regenerating spent dialysate in a regeneration chamber 14, and recirculating refreshed or regenerated dialysate to dialysis chamber 12. In the present system, spent dialysate may exit dialysate compartment 20 of dialysis chamber 12 through dialysis outflow 42. The spent dialysate then may flow (or be pumped) into regeneration chamber 14, as indicated by arrow D.

In contrast to the present system, in some systems, where the spent dialysate is refreshed by adsorption and reused, essential cations, such as $Ca^{2+}$, $Mg^{2+}$, $Na^{2+}$, and $K^+$, may be lost through adsorption on the sorbents. In such systems, the patient may be required to be provided with supplements to replenish the dialyzed essential cations.

Regeneration chamber 14 may be configured to regenerate purified dialysate. In the present system, regeneration chamber 14 may include various toxin traps. For example, in some embodiments, regeneration chamber 14 may include fibers as described in more detail below. These fibers may be capable of trapping, or retaining urea, uric acid, creatinine, and other toxins, and removing such toxins from the spent dialysate. Once the toxins are removed, the spent dialysate may be considered to be purified such that it is regenerated or refreshed dialysate. The toxin trap may further repel or ward off electrolytes, such as essential cations, from the trap, thus maintaining the cations in the refreshed dialysate. In some embodiments, the dialysate regeneration chamber may include, in addition to the toxin trap, one or more semi-permeable membranes. In other embodiments, the dialysate regeneration chamber may be configured without a semi-permeable membrane or the like.

The refreshed dialysate, or regenerated dialysate, with minimal concentrations of toxins, may exit the regeneration chamber 14 and flow (or be pumped) to dialysate reservoir 16, as indicated by Arrow E. Refreshed dialysate may be stored in dialysate reservoir 16, and when needed, may flow into dialysate compartment 20 of dialysis chamber 12, as indicated by arrow F. As such, the dialysate may be considered as reused within the system.

By regenerating dialysate, the dialysis system of FIG. 1 may eliminate or substantially reduce some of the inconveniences and costs associated with conventional dialysis treatments. For example, by regenerating dialysate, it may be possible to substantially reduce the amount of dialysate required to perform a dialysis treatment. Reduction of the amount of dialysate may substantially reduce the physical size requirements for a dialysis system, thus reducing the physical footprint of the dialysis machines. In some embodiments, the size requirements may be so reduced as to enable the dialysis system to be portable. By reducing the size of the dialysis system, a dialysis patient may have increased mobility, convenience and comfort. The portable dialysis machines may provide life changes to a dialysis patient, enabling the patient to travel, work and enjoy activities previously difficult to access using the prior treatment machines.

In addition to the patient's increased life choices, treatment facilities may also receive various benefits. For example, treatment facilities may be able to dedicate less floor area to the systems and provide more convenient and comfortable facilities for dialysis treatment.

Additionally, the refreshed dialysate may reduce the costs associated with dialysis, including reduction of costs related to purifying the large quantity of water needed with conventional systems, costs related to preparing and storing large amounts of dialysate, costs related to properly disposing large amounts of dialysate, costs related to maintenance of large dialysate machines, etc. For example, replacement of the small volume of dialysate in the present system may be substantially simpler, easier, quicker and more easily learned compared to prior systems. Thus, less time and effort may be needed to operate the dialysis machines and treat the dialysis patient. For example, time may be saved due to the substantial elimination of the draining and refilling process for the dialysate required in the earlier systems.

Figure 2:
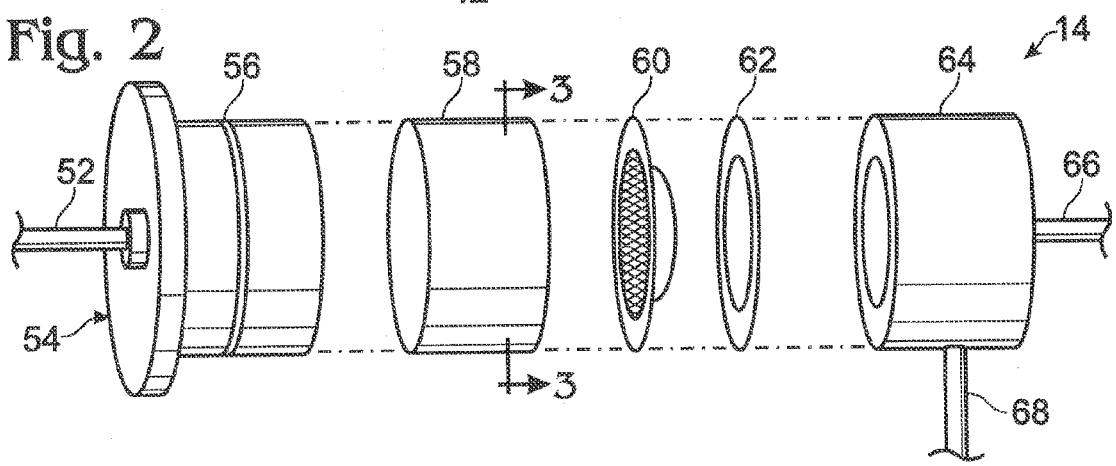
FIG. 2 is a schematic illustration of a dialysate regeneration cartridge for use in the exemplary system shown in FIG. 1 according to an embodiment of the present disclosure.

FIG. 2 is a schematic illustration of an exemplary dialysis regeneration chamber 14. Regeneration chamber 14 may be comprised of a housing having a spent dialysate inlet 52 and at least one refreshed dialysate outlet 66. The inlet and outlet may be part of a tubing system such that the regeneration chamber is interposed the dialysis chamber and the dialysate reservoir.

In the illustrated embodiment, dialysate inlet 52 is disposed in cartridge top 54. Cartridge top 54 may be configured to fit or couple to cartridge or chamber housing 64. Coupled with or contained in cartridge top 54 and cartridge housing 64 may be sealing devices, such as one or more O-rings 56 and/or gaskets, such as bottom gasket 62. Such sealing devices may be configured to maintain the system as a closed system and prevent leakage of dialysate from the housing.

Further contained within regeneration chamber 14 may be a dialysate regeneration fabric 58. This dialysate regeneration fabric may be configured to remove toxins from the dialysate while substantially maintaining the required levels of essential cations. In some embodiments, the regeneration chamber may further include a support screen 60.

As described above, spent dialysate (toxin-laden dialysate) may be introduced into the regeneration chamber through inlet 52. The spent dialysate may encounter the dialysate regeneration fabric 58. The toxins may be captured by the fabric and retained such that refreshed dialysate exits through regenerated dialysate exit 66. In some embodiments, the toxins may be retained within the fabric or along the screen. In other embodiments, a second outlet, such as elimination port 68, may be provided to remove the trapped toxins. Toxins may be released through the elimination port such that the toxins are not retained in either the regeneration chamber or recirculated back to a dialysis chamber in refreshed dialysate.

Figure 3:
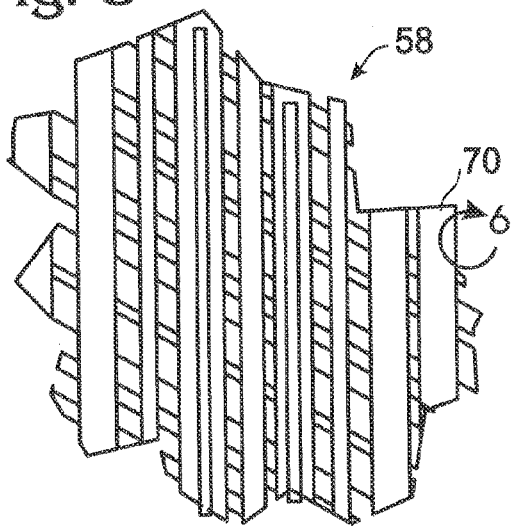
FIG. 3 is a cross-sectional view of an ion-selective fabric included within the dialysate regeneration cartridge taken along line 3-3 of FIG. 2.

FIG. 3 provides a schematic illustration of an enlarged cross-sectional view of the dialysate regeneration fabric 58 of FIG. 2, taken along line 3-3 of FIG. 2. Dialysate regeneration fabric 58 may contain one or more fibers, such as for example ion-selective fibers (ISF), or in some embodiments, ion-selective activated fibers (IS-AF) 70. The ion-selective fibers may be configured to selectively capture one or more toxins. Although described in relation to a single fiber, it should be appreciated that the fabric/fiber may include one or more fibers and such fabric/fibers may interact together to form a toxin trap.

It should be appreciated that any suitable fiber may be used. In some embodiments, the fabric may be composed of carbon fibers or other suitable fiber-like materials, including plastics, polymers, resins, silicone, etc. Further, in some embodiments, the fibers may be particles, aggregates, weaves, rings, tubes, such as nanotubes, etc. In some embodiments, the fibers may be acid-treated or oxidized, while in other embodiments, the fibers may be not acid-treated or oxidized.

Additionally, the fibers may be activated fibers or non-activated fibers. For example, in one embodiment, the fibers may be activated carbon fibers. Activated carbon fibers may be made by the carbonization and activation of precursor fibers (e.g. polyacrylonitrile, phenol resin, pitch, rayon, etc.) at high temperature and in the presence of an oxidizing gas such as oxygen, water, or carbon dioxide.

For example, activated carbon may be made by burning hardwood, nutshells, coconut husks, animal bones, pitch, carbon-containing polymers (such as rayon, polyacrylonitrile, etc.), and other carbonaceous materials. The charcoal becomes "activated" by heating it with steam, carbon dioxide, or carbon monoxide to high temperatures in the absence of oxygen. This heating removes any residual non-carbon elements and produces a porous internal microstructure with an extremely high surface area.

In one embodiment of the present disclosure, the ion-selective fibers may be ion-selective urease-immobilized fibers (ISUIFs), ion-selective urease-immobilized activated fibers (ISUI-AFs), or urease-immobilized poly-ether sulfone membrane (or any other polymer membranes or polymers) with ion-selective fiber, or a combination of the above. Alternative embodiments may include traps selective for other waste products to be dialyzed including, but not limited to, phosphate.

Any suitable fabric may be used for dialysate regeneration fabric 58. The ion-selective fibers 70 may be disposed in any orientation, and although shown in an overlapping, bi-parallel orientation, it should be appreciated that they may be oriented in a variety of patterns, including a chaotic arrangement. Fibers 70 may be uniform or variable sizes within fabric 58. Although, not illustrated in FIG. 2, immobilized enzymes, such as urease, may be disposed along the fibers for use in decomposition of urea. Other select enzymes, for decomposition and/or trapping of other toxins, may also be selectively disposed along the fibers. Also, the enzymes may be a urea trap instead of ammonium trap.

Fibers 70 may be commercially available activated fibers (AF). In some embodiments, activated carbon fibers (ACF) and fabrics are used. One exemplary fiber for use in the dialysis system described herein may be K5d25. K5d25 is a basket weaved fiber with a density of 250 g/m$^2$ and a specific surface area of 2,500 m$^2$. Although an exemplary fiber is provided, other fabrics and fibers may be used without departing from the scope of the disclosure. For example, other commercially-available fibers or prepared fibers/fabric may be used.

It should be noted that the fibers may have a three-dimensional configuration. Within the three dimensional configuration, the fibers may be disposed such as to form micropores, or structures that may contain select functional groups. Such structures may be configured to trap or retain select ions. For example, the pores may be charged to selectively trap oppositely-charged ions. In one example, the pores may be negatively charged, thus configured to attract and trap positively-charged ions, such as ammonium.

Once a fabric is selected, the fabric fibers may be prepared for use as the dialysate regeneration fabric. In some embodiments, the fiber surface may be modified to increase the concentration of oxygen-containing functional groups. The modification to the surface may be such that the surface of the fiber is oxidized. For example, the surface may be modified by the addition of carboxylic acid groups and hydroxyl groups.

Any suitable method may be used to modify the surface, including, but not limited to, heat treatments, peroxide treatments, acid treatments, etc. Modification of the surface of the fiber to include high oxygen concentration and higher relative concentration of carboxylic and hydroxyl groups may provide the functional groups for ammonium binding and enable further modification of the fiber. It should be appreciated that surface, as used herein, may be any portion of the fiber that may be exposed or exposable to the dialysate or any portion of the dialysate.

Although any suitable method may be used to modify the surface of the fiber, the following tables show exemplary results after various surface modification methods. Specifically, in Table 1, fiber samples were individually treated to increase the concentration of oxygen-containing functional groups on the surface. As shown, the acid-treated fiber had the highest atomic percent of oxygen relative to the other treated fibers. However, it should be appreciated that the other treatments, as well as other surface modification methods, may be appropriate to prepare the fiber surface for ammonium binding and/or subsequent modification.

TABLE 1

Elemental Composition of Fiber Samples (ACF)

| | Atomic Percent | | |
|---|---|---|---|
| Sample | C | O | N |
| Untreated | 97.1 | 2.9 | nd |
| Heat Treatment | 96.5 | 3.5 | nd |
| Peroxide Treatment | 91.1 | 6.2 | 2.6 |
| Acid Treatment | 85.3 | 13.1 | 1.5 | nd = none detected

Table 2 further illustrates the relative concentration of oxygen-containing functional groups on modified fiber samples. Again, it should be appreciated that other methods may be used to modify the fiber surface.

TABLE 2

Relative Concentration of Oxygen-containing Functional Groups on Modified Fiber Samples (ACF) compared to Untreated Sample.

| | Fiber Sample | |
|---|---|---|
| Carbon species | Peroxide Treatment | Acid Treatment |
| Ether/alcohol | 51.0 | 45.0 |
| Aldehyde/ketone | 23.5 | 24.7 |
| Carboxylic | 25.4 | 30.3 |

Figure 4:
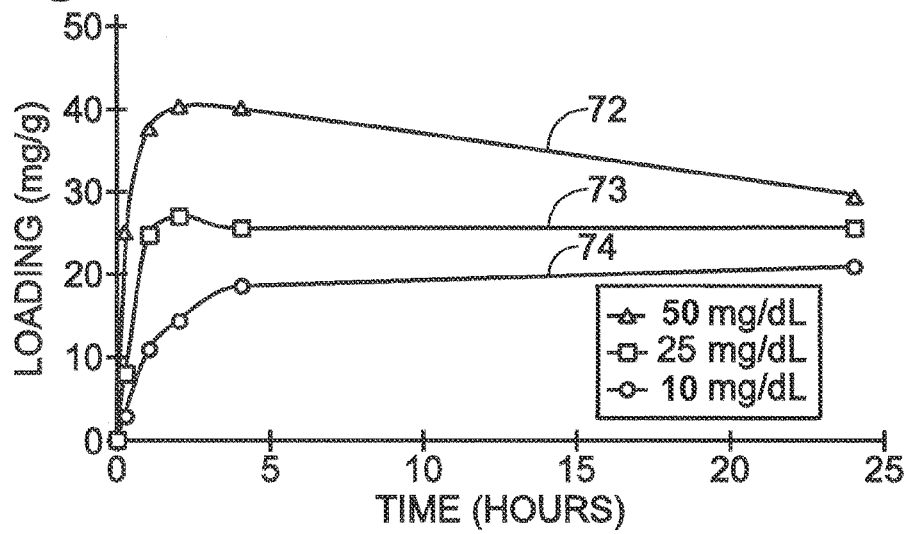
FIG. 4 is a graph illustrating the ammonium binding capacity of an acid-treated fiber for use in the dialysate regeneration cartridge of FIG. 2.

Referring now to FIG. 4, the surface-modified fiber may be capable of binding ammonium. FIG. 4 illustrates ammonium binding to a surface-modified fiber, specifically ammonium binding to an acid-treated activated fiber. FIG. 4 provides results where surface-modified activated fiber samples were incubated in solutions containing ammonium hydroxide of three different concentrations (10 mg/dL, 25 mg/dL and 50 mg/dL), with shaking at 33° C. for 0 to 24 hours. Following incubation, the remaining ammonium concentrations in the supernatant solutions were measured to determine the amount of ammonium ions bound to the fiber by a modification of the Berthelot method, and the results graphed in FIG. 4. Line 72 is a plot of the results obtained from an acid-treated activated fiber incubated in the 50 mg/dL ammonium hydroxide solution, Line 73 is a plot of the results obtained from an acid-treated activated fiber incubated in the 25 mg/dL ammonium hydroxide solution, and Line 74 is a plot of the results obtained from the an acid-treated activated fiber incubated in the 10 mg/dL ammonium hydroxide solution.

The fibers, such as surface-modified fibers described above, may be of sufficient physical strength to be subject to various dialysate circulation flows. For example, in one test, no detectable carbon particles were dissociated when the fibers were subjected to the circulating dialysate. Thus, the fibers may be durable for use in the regeneration chamber.

An ion-barrier further may be constructed on the surface of the fibers. Any suitable ion-barrier may be constructed, for example, and not as a limitation, an ion barrier may be prepared by attachment of a long chain hydrocarbon moiety onto the surface of the fiber. Any suitable hydrocarbon moiety may be used, including a lipid or fatty acid which may be attached onto the surface of the fiber. The attached lipid barrier, such as a lipid chain, ring, etc. may create a physical barrier to the internal surface of the fabric. Any suitable fatty-acid chain or the like may be used for attachment onto the fiber.

Although other suitable ion barriers may be prepared on the fiber, the following method of constructing an ion barrier on the activated fiber is provided for illustrative purposes. Specifically, in one embodiment, a surface-modified activated fiber, such as an acid-treated activated fiber, may be further modified to create an ion barrier by addition of a fatty acid. The fatty acid may be as short as C4 or may extend to C25. In some embodiments, fatty acids with chain lengths of C14 to C17 may be used. It is noted that the carbon of the carboxyl group of the fatty acid is counted when discussing the number of carbons in the fatty acids.

In an exemplary embodiment, an ion-barrier may be constructed on the activated fiber by reacting a surface-treated activated fiber, such as an acid-treated activated fiber, with palmitoyl chloride in the presence of an acid scavenger, such as pyridine, triethylamine, 4-(dimethylamino)pyridine, Proton-Sponge®, and several polystyrene-divinylbenzene (PS-DVB)-supported acid scavengers including several PSDVB-supported piperidine compounds. The reaction may result in addition of palmitoyl groups (C16) attached to the activated fiber. It should be appreciated that any other suitable carbon chain or carbon barrier may be attached to the activated fiber, in addition to, and/or alternatively to, the palmitoyl groups.

Further the fibers may be modified to include both an ion barrier and immobilized urease enzyme or other desired immobilized enzyme. The immobilized urease enzyme may be configured to decompose urea into ammonium ions. The ammonium ions may be trapped by the fabric. For example, the positively-charged ammonium ions may be attracted to the fabric by the negative charge of the fibers.

Any suitable method may be used to immobilize the selected enzyme. In some embodiments, it may be selected to covalently attach urease, or other suitable enzyme, to the fiber. Any suitable biochemical methods may be used to attach or otherwise immobilize the select enzyme or enzymes.

As an illustrative example, in one embodiment, purified urease may be immobilized onto the ion-selective activated carbon fiber by using the combination of 8-aminocaprylic acid linker and a glutaraldehyde linker. In the initial coupling reaction to attach the linker to the AF, 1-(3-dimethylaminopropyl)-3-ethyl-carbodiimide hydrochloride (EDC) may be used as a coupling reagent. It may be appreciated that other coupling agents, and/or covalent linkers, as well as other biochemical methods, may be used to immobilize urease, or an alternative ion-selective compound, onto the fiber.

An example preparation of an ion-selective urease-immobilized fiber is provided below:

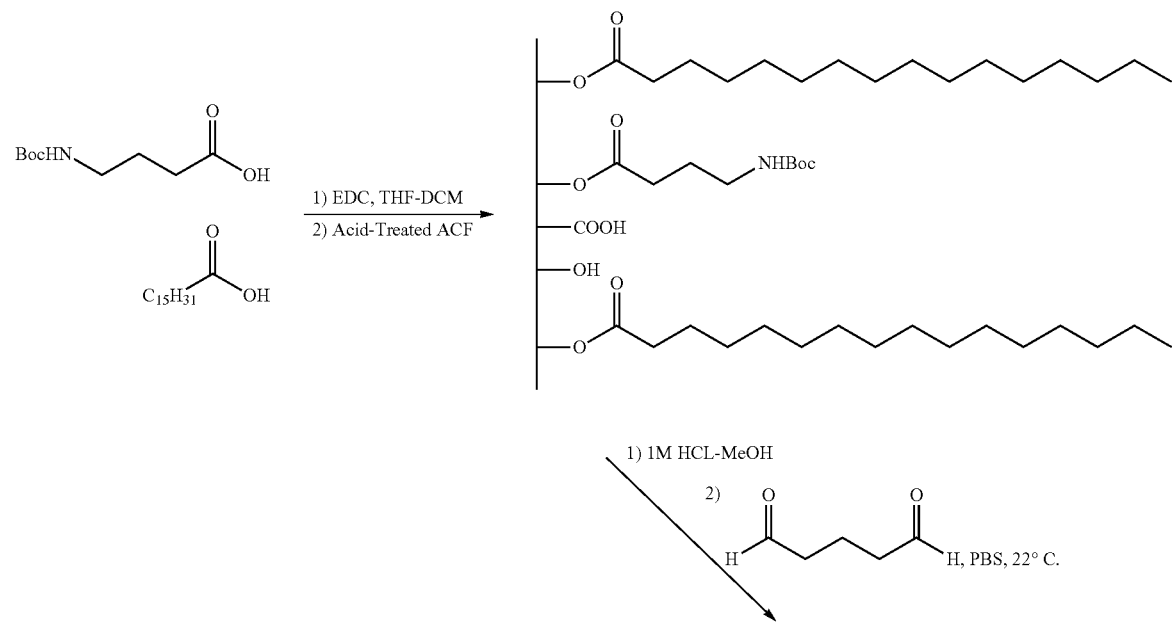

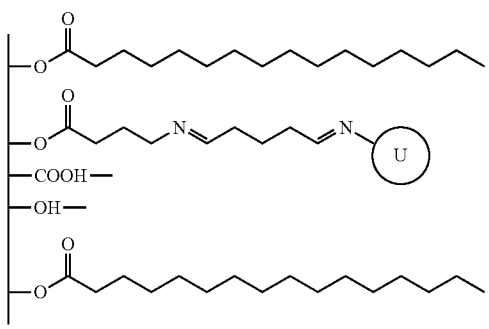 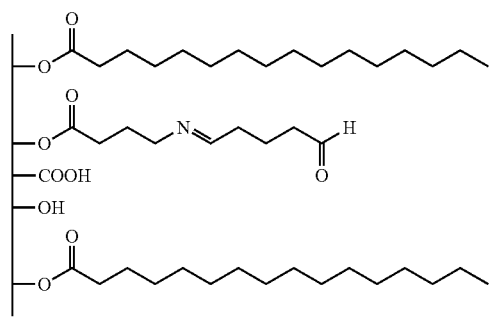

Figure 5:
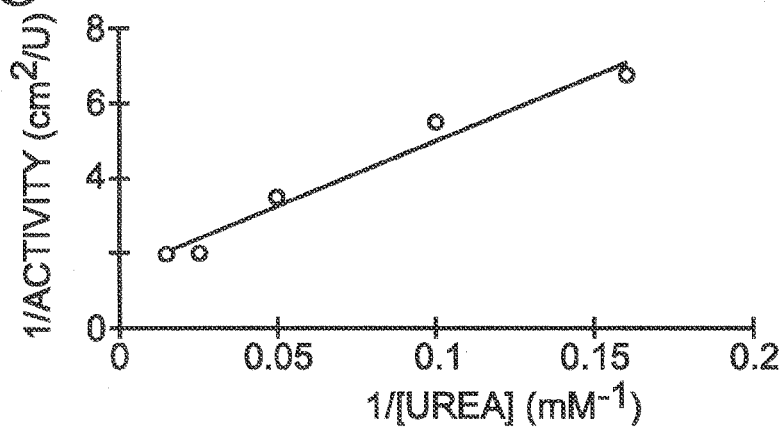
FIG. 5 is a graph illustrating the activity of urease immobilized on an activated fiber for use in the dialysate regeneration cartridge of FIG. 2.

The immobilization of urease on the fibers enables degradation of urea within the spent dialysate. As an example, FIG. 5 illustrates kinetic studies performed to study characteristics of the urease when immobilized onto an ion-selective urease-immobilized ACF. The enzyme kinetic studies were performed under the standard steady-state kinetics. The experimental data were analyzed using a Lineweaver-Burk plot. In this example, the calculated $K_m$ value and $V_{max}$ values were 22.8 mM and 0.65 µmol/min/cm$^2$, while simultaneously, the $K_m$ and $V_{max}$ values of free urease, were determined to be 5 mM and 0.1 µmol/min. Thus, although the immobilized urease may have a lesser affinity toward urea, it may have a higher catalytic activity than free urease. Thus, although the urease is immobilized, it retains sufficient activity to degrade urea contained within the spent dialysate. It should be appreciated that the $K_m$ and the $V_{max}$ may differ depending on experimental conditions, bonding conditions, reaction conditions, etc.

As described above, in one exemplary embodiment, the synthesized dialysate regeneration fabric may include one or more fibers with one or more of the following: a hydrophobic layer adjacent to attached lipid chains, an ion-selective barrier formed by the lipid chains, immobilized urease capable of catalyzing the hydrolysis of urea to ammonia ions and other chemical reaction intermediaries, and hydrophilic pores capable of trapping other toxins. These portions of the dialysate regeneration fabric are further discussed below in reference to FIG. 6.

Although preparation of the fiber is discussed in a step-by-step process, it should be appreciated that the steps may be reversed or accomplished in any suitable order. Moreover, in some embodiments, construction of an ion-selective, urease-immobilized fiber may be accomplished using more or less steps than described herein. It is appreciated that various biochemical methods to generate such an ion-selective, urease-immobilized, activated carbon fiber (and other like fibers) may be used to generate the dialysate regeneration fabric and any examples provided are illustrative and not limiting in any sense.

Figure 6:
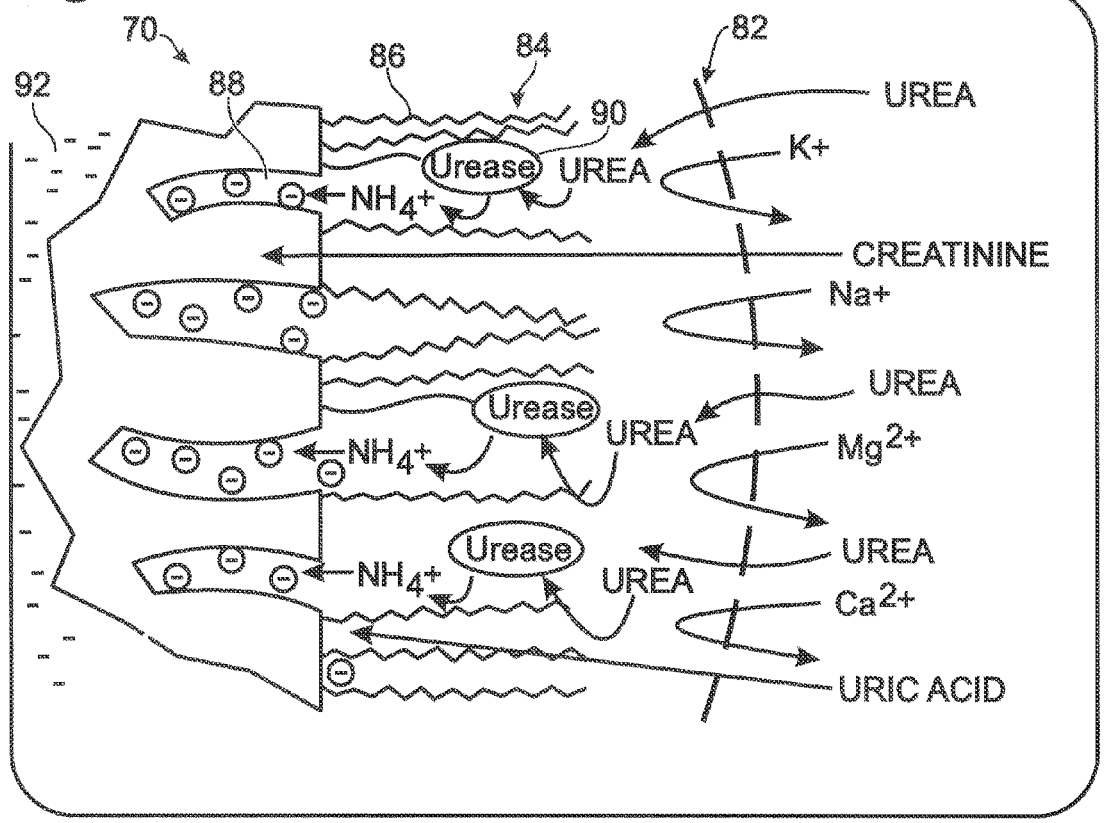
FIG. 6 is a schematic enlargement of an ion-selective urease-immobilized fiber, taken along arrow 6 of FIG. 3, illustrating molecule movement and entrapment of toxins within the ion-selective urease-immobilized fabric.

Referring now to FIG. 6, a schematic enlargement of an ion selective fiber of FIG. 3 is provided. FIG. 6 provides a schematic illustration of molecule movement and entrapment within the ion-selective urease-immobilized fiber, generally indicated at 70. The illustrated fiber/fabric 70 may be provided within the dialysate regeneration fabric of regeneration chamber 14 of FIGS. 1 and 2.

As an overview, when spent dialysate enters regeneration chamber 14, and contacts fiber 70 the uremic toxins may be removed from the dialysate and trapped in the fibers, while electrolytes, such as essential cations, may be selectively retained in the regenerated dialysate. Referring to FIG. 3, the spent dialysate includes urea and other toxins, including creatinine and uric acid. The dialysate further includes various essential cations, including, but not limited to, $K^+$, $Na^+$, $Mg^{2+}$, and $Ca^{2+}$. Fiber 70 acts as and is configured as a toxin trap.

Specifically, when toxins, such as urea, uric acid, creatinine, etc. engage the fiber, the toxins are trapped within the fiber such that the spent dialysate is refreshed. However, the trapping of the essential cations is minimized such that a substantial amount of essential cations remain with the dialysate. In other words, the essential cations may be considered as repelled from the trap such that a substantial number of cations remain in the dialysate and this cation-present, substantially toxin-free dialysate may be understood to be refreshed dialysate. Thus, this refreshed dialysate may be used in a dialysis system without use (or minimal use) of cation supplements.

Referring now more specifically to the ion movement around fabric 70, spent dialysate enters the regeneration chamber with a mixture of essential cations ($K^+$, $Na^+$, $Mg^{2+}$, and $Ca^{2+}$), and toxins, including urea, creatinine, uric acid and other small uremic toxins. The spent dialysate may encounter a hydrophobic semi-permeable membrane 82. The various components of the spent dialysate may be able to flow across the semi-permeable membrane 82 to engage the fabric.

As described above, fiber 70 may be prepared such that it includes an ion-selective barrier or hydrophobic barrier, indicated at 84. Ion-selective barrier 84 may include fatty acid chain extensions 86 with carbon chains of C4-C25. The carbon chains may extend away from the body of the fabric to form a physical barrier to cations, such as $K^+$, $Na^+$, $Mg^{2+}$, and $Ca^{2+}$. It should be noted that such cations may be of an increased size due to hydration. Thus, although the fiber may be charged such that various ions are attracted to the fiber, some large molecules (such as the hydrated cations) may be prohibited from entering into the fiber by the fatty acid chain extensions. Thus, the chains may operate as an ion-selective barrier, allowing small molecules to pass through into the fiber, (thus trapping the small molecules within the fiber), while physically preventing the larger molecules (such as the hydrated cations) from passing though to the trap.

The hydrophobic nature of the ion-selective barrier must be balanced with the accessibility of urea to the immobilized urease. Thus, the barrier must be sufficiently hydrophobic to repel the essential cations, but be not so hydrophobic as to significantly decrease the rate of diffusion of urea to urease.

For example, in the illustrated embodiment, essential cations, such as $K^+$, $Na^+$, $Mg^{2+}$, and $Ca^{2+}$ may be substantially unable to penetrate the physical barrier presented by the carbon chains. The essential cations may be considered to be repelled from the ion selective hydrophobic barrier. Thus, the essential cations are retained in the dialysate, thereby maintaining ionic homeostasis in the dialysate during dialysis treatment.

However, toxins, such as creatinine and uric acid, may be able to penetrate the barrier and thus may be readily adsorbed by the fiber. The toxins become trapped within the barrier. The chains may also be configured to allow urea to pass through and be trapped by the barrier. Moreover, ammonium ions, which result from the break down of urea, may be attracted to the negatively charged fiber and trapped, thus preventing the ammonium ions from reentering the dialysate.

It should be appreciated that in some embodiments the carbon chains may be of different sizes along the length of the fiber or the fabric. In other embodiments, the carbon chains may be of the same length along the fiber or fabric. The position of the chains may be dependent on the effectiveness of the barrier. Moreover, in some embodiments, where shorter length chains are utilized, the shorter length chains may be positioned in relatively close proximity, while, in other embodiments, longer length chains may be more separated. Such spacing may be effective as the longer chains may cover more area and provide an appropriate physical barrier without being as closely positioned as shorter length chains. Further, although shown as extended carbon chains, in some embodiments, the chains may include one or more rings, or other configurations, such that the carbon chains are considered a carbon barrier.

As discussed above, fabric 70 further may include hydrophilic pores 88. These hydrophilic pores may be sufficiently charged to attract oppositely charged ions. For example, the hydrophilic pores may be negatively charged, thus attracting positively-charged ammonium and trapping the ammonium within the fiber. It should be noted that in some embodiments, an ion exchange resin 92 may be provided. For example, a negatively-charged ion exchange resin may be provided to increase the negative charge along the fiber. Thus, ensuring attraction and trapping of select ions.

As described above, fiber 70 may further include immobilized enzymes, such as urease, indicated at 90. Although urease is described as the immobilized enzyme, any suitable enzyme may be used or provided in the traps. In this example, the immobilized urease may be configured to hydrolyze urea. The resulting ammonium ions, $NH_4^+$ may be attracted by the negative charge of the fiber 70 and may be trapped inside of the barrier and adsorbed by the hydrophilic pores of the fiber.

As described above, the present system provides that a toxin trap is within a dialysate regeneration chamber. Spent dialysate may enter the regeneration chamber and engage the dialysate regeneration fabric which is configured to refresh the dialysate. The dialysate regeneration fabric may be considered a toxin trap: selectively trapping uremic toxins, such as creatinine, uric acid, and phosphate and selectively degrading urea, such that the resultant ammonium ions are subsequently trapped. Non-toxins, such as essential cations, may be substantially immune from the toxin trap, thus remaining within the dialysate. The substantially toxin-free dialysate (refreshed dialysate) may be recycled to the dialysate reservoir 16 for reuse in the dialysis chamber 12.

Figure 7:
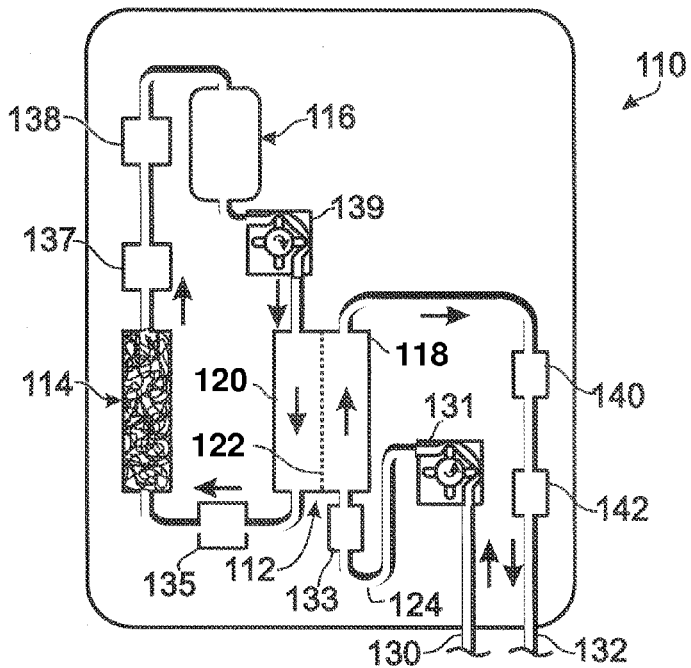
FIG. 7 is a schematic illustration of another embodiment of a dialysis system in accordance with the present disclosure.

FIG. 7 provides another illustration of a dialysis system (indicated generally at 110) in accordance with an embodiment of the present disclosure. Dialysis system 110 is shown as a portable hemodialyzer. The system utilizes the above-discussed dialysate regeneration fabric such that the dialysate may be refreshed and reused. Reuse of the dialysate enables the system to be portable, cost-effective and more easily used by dialysis patients.

Similar to system 10 in FIG. 1, dialysis system 110 may include a dialysis chamber 112 having a blood compartment 118 and a dialysate compartment 120. A semi-permeable membrane 122 may separate the two compartments. Dialysis system 110 further may include a dialysate regeneration chamber 114 and a dialysate reservoir 116.

Operation of system 110 may include input of high toxin concentrated blood (uremic blood) though input tube system 130. In some embodiments, the uremic blood from the patient may be pumped by a blood pump 131 to blood compartment 118 of the dialysis chamber 112. Various blood flow sensors, 133 and 140, may be provided to regulate and monitor blood flow. Further, one or more air bubble sensors, such as air bubble sensor 142 may be provided.

In some applications, when the weight of the system is critical, some sensors, such as gas monitors may be omitted from the full system hemodialyzer. Alternative sensing methods may be used. For example, blood samples from patients may be periodically collected with use of a 3-way lumen and the concentration of cations, ammonium, urea, uric acid, creatinine, phosphate, oxygen, bicarbonate, glucose, pH, etc. may be determined using any suitable portable analysis system.

Semi-permeable membrane 122 may separate the blood from the dialysate fluid in the dialysate compartment 120. The semi-permeable membrane within the dialysis chamber may allow specific uremic toxins to flow from the patient's blood across the membrane into the dialysate. As the dialysate becomes saturated with toxins, the spent dialysate may be passed to the regeneration chamber 114. The dialysate flow may be regulated by a dialysis flow sensor 135.

The spent dialysate is received within the regeneration chamber such that the toxin-laden dialysate engages the dialysate regeneration fabric. The dialysate regeneration fabric may include ion-selective, urease-immobilized fibers which trap the various toxins, removing them from the dialysate. The refreshed dialysate may exit the regeneration chamber and be sampled and examined for residual ammonia by an ammonia sensor 137. Additionally, multiple and specific blood gas parameters may be sampled and examined by a blood-gas analyzer 138 as the refreshed dialysate is pumped to the dialysate reservoir 116. The refreshed dialysate may be pumped from the dialysate reservoir, as needed, by a dialysate pump 126 back to the dialysis chamber 112 where the closed loop dialysis system and process may be repeated.

As described above, various sensors may be used to monitor multiple dialysis factors, including, but not limited to: blood flow rate, dialysate flow rates, temperature, oxygen levels, presences of air bubbles in the blood line, and dialysate composition, including cation, ammonia, bicarbonate concentrations, etc. In some embodiments, redundant sensors may be employed to ensure accuracy. A computer (not shown) may be used to receive information from the sensors, control the pumps, and record the relevant data. Although not shown, it should be appreciated that various electronics may be provided within the dialysis system to further control and monitor the dialysis process. Moreover, a user interface may be provided such that a user may have immediate information regarding the controls, sensors, and system control inputs.

It should be noted that in the disclosed system both blood and dialysate are pumped through their respective systems. In some embodiments, the pumps may be roller pumps, while in alternative embodiments, the pumps may include air pumps, electrical pumps, manual pumps, or any combination thereof. In some embodiments, the pumps may be capable of adjusting to flow rates in the range of 100-1000 ml/min.

In some embodiments, the dialysate reservoir or storage tank may have a capacity of approximately 6 L and may be easily accessible for filling, draining, and cleaning. By providing the closed loop, reuseable dialysis system, the weight of the dialysis system may be minimized such that the system may be lightweight enough to be portable. For example, the system may be sufficiently lightweight to enable the system to be manually carried.

In some embodiments, one or more of the dialysis system components may be disposable and replaceable. For example, in one embodiment, the entire dialysate and blood contact unit—tubing system 124, dialysis chamber 112, regeneration chamber 114 and dialysate reservoir 116—may be removed from the sensors and pumps for replacement. Alternatively, in some embodiments, regeneration chamber 114 may be selectively detachable from one or more components of the dialysis system such that regeneration chamber 114 (and the associated components) may be replaceable as a separate unit or combined component units.

In even other embodiments, regeneration chamber 114 may be manually detached from the tubing system, sensors, and other dialysis components and discarded and replaced with a new regeneration chamber. Thus, the regeneration chamber 114 may be considered a replaceable cartridge. As another alternative, the removed regeneration chamber may be dismantled to replace one or more disposable components housed within the regeneration chamber, such as the ion-selective fabric (shown as 58 is FIG. 2), or the support screen (shown as 60 in FIG. 2). Once the disposable regeneration chamber component is replaced with a new component, the regeneration chamber housing may be closed and the regeneration chamber may be reattached to its original location in the dialysis system.

It should be appreciated that although the dialysate regeneration chamber and associated fabric is described for use in a hemodialyzer or hemodialysis system, the dialysate regeneration chamber and associated fabric may be used in any dialysis system, including use in a peritoneal dialysis unit or system. Further such a regeneration chamber and associated fabric may be used in other systems that require removal of toxins from a fluid.

Referring now to FIGS. 8-13, various characteristics of the dialysate regeneration fabric are described. For ease of discussion, various experiments are described. It should be appreciated that such discussion is provided for illustrative purposes and is not intended to be limiting in any way.

Figure 8:
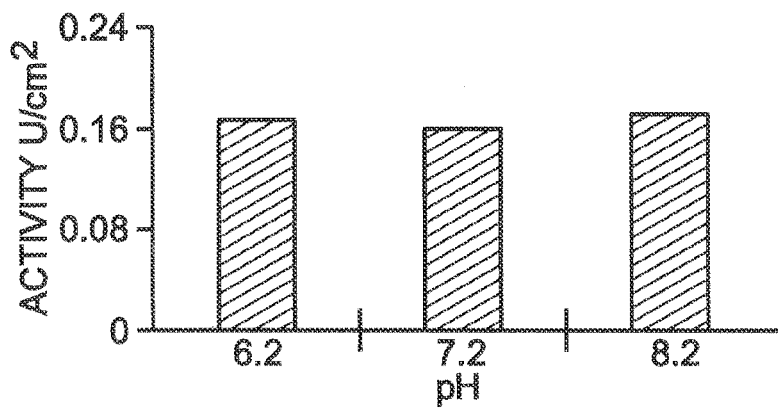
FIGS. 8-13 are graphs illustrating various characteristics of ion-selective, urease-immobilized, activated fibers for use in the dialysate regeneration cartridge of FIG. 2.

Referring to FIG. 8, a bar graph is provided showing the pH stability of urease in a sample ion-selective, urease-immobilized ACF. As shown, no significant decrease in urease activity was found at the pH levels tested.

Figure 9:
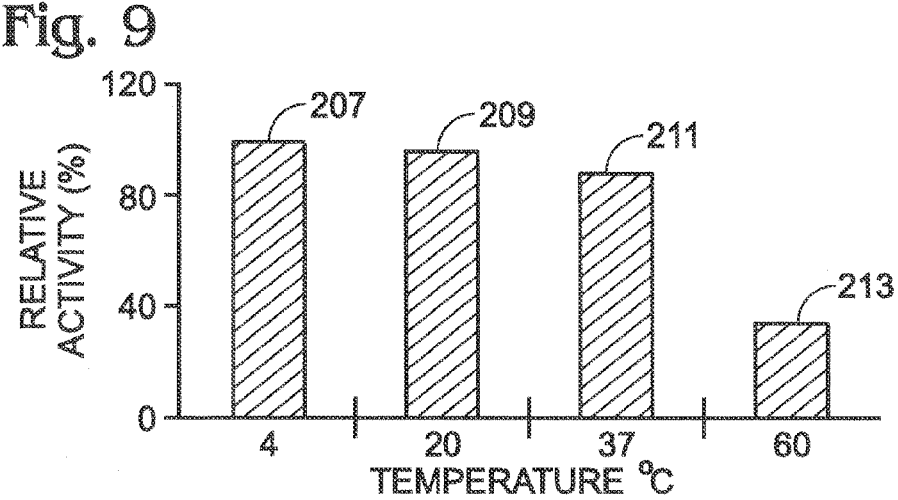

FIG. 9 illustrates the temperature stability of a test sample of an ion-selective, urease-immobilized ACF. As shown, the immobilized urease maintains its activity level at various operating temperatures. Thus, enabling use of the system in various temperature conditions.

Both the pH and temperature of a test sample of an ion-selective, urease-immobilized ACF were studied over extended time periods. Test results found that there was no significant decrease in urease activity during the extended tested time periods of 4 to 8 hours. Use of the portable dialysis system described herein may be significantly less than the tested extended time period, therefore ensuring that the urease activity is retained throughout the dialysis process.

Figure 10:
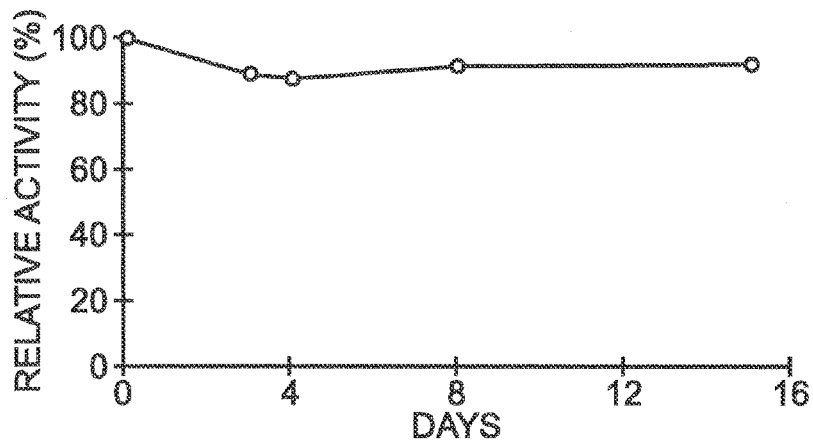

FIG. 10, further illustrates the stability of urease in a test sample of an ion-selective, urease-immobilized ACF over an extended period of time. As shown, the urease retained over 90% activity during storage in the wet state for 14 days at 4° C. By providing extended storage periods, a user or facility may be able to more easily store replacement regeneration chambers, or the like.

Figure 11:
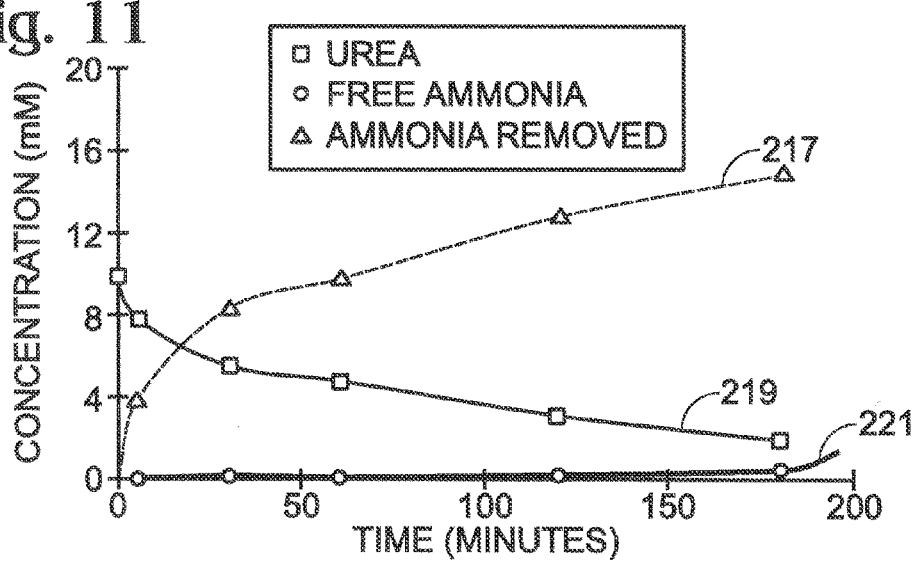

FIG. 11 illustrates the capacity of an ion-selective, urease-immobilized ACF to eliminate urea in terms of hydrolysis of urea and adsorption of produced ammonium ion using an appropriate dialysate buffer. As shown, Plot 217 is the concentration (mM) of the ammonia removed from dialysate over time (minutes), Plot 219 is the concentration of the urea in the dialysate over time, and Plot 221 is the concentration of the free ammonia in the dialysate over time. As illustrated, the sample ion-selective, urease-immobilized ACF efficiently removed the urea in the dialysate. The free ammonium ion produced by urease was negligible under the detection method (Berthelot) employed in this assay indicating that the urea travels across the ion-selective layer to reach urease in the fiber, but the highly charged ammonium ions that are formed cannot leave the fiber due to the ion-selective layer, and are efficiently adsorbed by the fiber.

Figure 12:
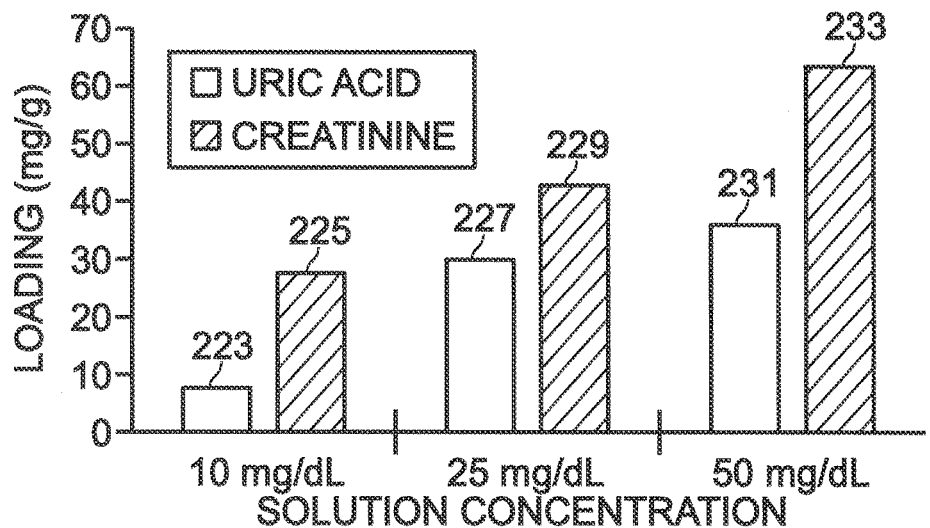

FIG. 12 further illustrates the effective removal of uremic toxins, such as creatinine and uric acid using ion-selective activated carbon fibers. Specifically, FIG. 12 illustrates the adsorption of varying concentrations of uric acid and creatinine at 33° C. Bar 223 is the adsorption (loading, mg/g) of uric acid at a concentration of 10 mg/dL and bar 225 is the adsorption of creatinine at a 10 mg/dL solution; bar 227 is the uric acid adsorption at a 25 mg/dL solution and bar 229 is the adsorption of creatinine at a 25 mg/dL solution; and bar 231 is the uric acid adsorption at a 50 mg/dL solution and bar 233 is the adsorption of creatinine at a 50 mg/dL solution. Thus, as shown, both the uric acid and the creatinine are adsorbed into the fabric at appropriate levels to not necessitate additional components to remove such toxins. However, it should be appreciated, that in some systems, components may be included to enhance absorption or capture of these toxins.

Figure 13:
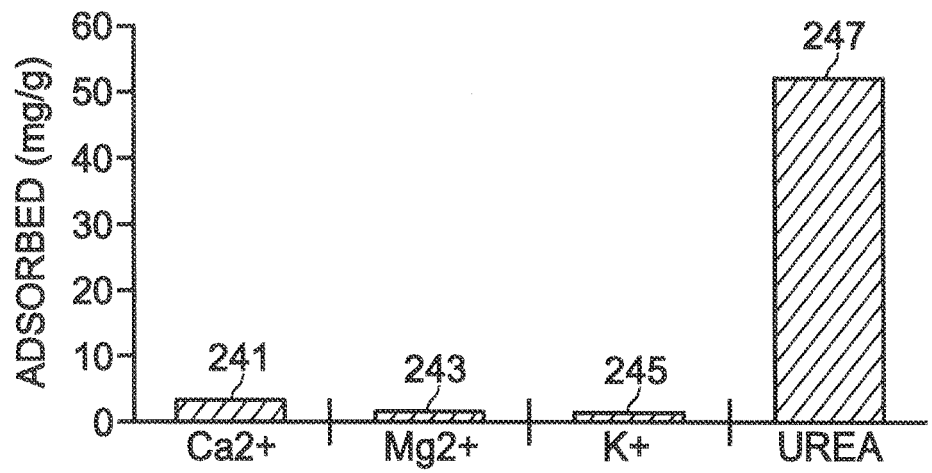

Referring now to FIG. 13, the ion-selective activated fiber is shown to repel cations in dialysate. In the illustrated test, ion-selective activated carbon fibers were incubated in a solution containing ions at physiological concentrations (1.5 mM $CaCl_2$, 140 mM NaCl, 1.0 mM KCl, and 0.5 mM $MgSO_4$) for 24 hours at 35° C. with shaking. The reductions in ion concentrations were 0.33% for $Ca^{2+}$, 0.83% for $Mg^{2+}$, approximately 3% for Na+ and 0.25% for $K^+$. The data were used to calculate the ion adsorption capacity of the fibers, where bar 241 graphs the adsorbed (mg/g) $Ca^{2+}$, bar 243 graphs the adsorbed $Mg^{2+}$, and bar 245 graphs the adsorbed $K^+$. As illustrated, the ion-selective fiber repels the essential cations, thereby maintaining the cations within the dialysate for reuse. It is noted, that the urea, even without the immobilized urease, was substantially adsorbed onto ion-selective ACF. As such, it should be noted that urea, like the other toxins, passes through the ion-selective barrier, in contrast to the essential cations.

It should be appreciated that in some systems, the removal of urea may be less critical. In such systems, the toxin traps may have little or no immobilized urease. Further such systems may be designed without a cation exchanger. For example, the ion-selective fabric/fiber may be less hydrophobic and may be constructed with non-oxidized fibers.

Thus, the above toxin traps may be used to trap other types of toxins, including pathogens, viruses, bacteria, etc. In these systems, the traps may include an alternative adsorbent, specific to trap the select toxin. For example, such a system may be applied to reduce or minimize the presence of toxins, including pathogens, viruses, bacteria, etc. in patients under acute infections, as well as patients under exposure to pathogenic viruses and bacteria. Moreover, patients with exposure to organic toxins as well as toxic heavy metals may be treated with the above toxin trapping system. In other words, the toxin traps may be used as a tool for hemofiltration.

Although the present disclosure includes specific embodiments, specific embodiments are not to be considered in a limiting sense, because numerous variations are possible. The subject matter of the present disclosure includes all novel and nonobvious combinations and subcombinations of the various elements, features, functions, and/or properties disclosed herein. The following claims particularly point out certain combinations and subcombinations regarded as novel and nonobvious. These claims may refer to "an" element or "a first" element or the equivalent thereof. Such claims should be understood to include incorporation of one or more such elements, neither requiring, nor excluding two or more such elements. Other combinations and subcombinations of features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

I claim:

1. A method of generating a toxin trap, the method comprising:
   heating a precursor fiber to form an activated carbon fiber and acid-treating the activated carbon fiber to form a surface-modified activated carbon fiber;

immobilizing an enzyme on the surface-modified activated carbon fiber;

providing an ion exchange resin coupled to the activated carbon fiber; and attaching a fatty acid to the surface-modified activated carbon fiber by reacting the surface-modified activated carbon fiber with the fatty acid in the presence of an acid scavenger to generate an ion-selective barrier, wherein the fatty acid extends away from a body of a fabric including the activated carbon fiber, where the fatty acid attached to the activated carbon fiber forms a physical barrier to cations excluding the cations from trapping while selectively trapping toxins.

2. A regeneration cartridge made in accordance with the method of claim 1.

3. The method of claim 1, further providing immobilizing a urease on the activated carbon fiber.

4. The method of claim 1, wherein the fabric is a dialysate regeneration fabric and the toxins are prevented from passing into refreshed dialysate.

5. The method of claim 4, further comprising positioning the fabric in a regeneration chamber, providing an inflow configured to admit a toxin-laden fluid into the regeneration chamber and providing an elimination port configured to release toxins from the regeneration chamber.

6. The method of claim 4, further providing an ion exchange resin coupled to the activated carbon fiber wherein the ion exchange resin is negatively charged.

7. The method of claim 4, further comprising providing immobilized urease on the activated carbon fiber.

8. The method of claim 4, further comprising providing an outflow to release non-toxin-laden fluid.

9. The method of claim 4, further comprising in addition to the fabric, a hydrophobic semi-permeable membrane, both within a dialysate regeneration chamber, the semi-permeable membrane positioned within the dialysate regeneration chamber such that spent dialysate entering the chamber flows across the semi-permeable membrane to engage the fabric.

10. The method of claim 4, further comprising providing hydrophilic pores within the dialysate regeneration fabric.

11. The method of claim 1 further comprising routing blood through a blood compartment of a dialysis chamber, the blood compartment separated from a dialysate chamber by a semi-permeable membrane; and routing dialysate from the dialysate chamber through a dialysate regeneration chamber, the dialysate regeneration chamber comprising the fabric, wherein the dialysate regeneration chamber is coupled to the dialysis chamber via a conduit.

12. The method of claim 11, wherein routing dialysate from the dialysate chamber through the dialysate regeneration chamber further comprises removing toxins in the dialysate by the fabric to form refreshed dialysate.

13. The method of claim 12, further comprising retaining essential cations in the refreshed dialysate.

14. The method of claim 13, wherein the essential cations include $Ca^{2+}$, $Mg^{2+}$, $K^+$, or $Na^+$.

15. The method of claim 12, further comprising releasing the toxins removed by the dialysate regeneration fabric via an elimination port.

16. The method of claim 1, wherein the fatty acid has a carbon chain length from 4 to 25.

17. The method of claim 1, wherein the fatty acid has a carbon chain length of 14 to 17.

* * * * *